United States Patent
Pein

(10) Patent No.: US 8,328,831 B2
(45) Date of Patent: Dec. 11, 2012

(54) WATER-JET DEVICE FOR SEPARATING A BIOLOGICAL STRUCTURE

(75) Inventor: Andreas Pein, Einhaus (DE)

(73) Assignee: Human Med AG, Schwerin (DE)

( * ) Notice: Subject to any disclaimer, the term of this patent is extended or adjusted under 35 U.S.C. 154(b) by 638 days.

(21) Appl. No.: 10/561,725

(22) PCT Filed: Jun. 18, 2004

(86) PCT No.: PCT/DE2004/001243
§ 371 (c)(1),
(2), (4) Date: Mar. 8, 2007

(87) PCT Pub. No.: WO2004/112623
PCT Pub. Date: Dec. 29, 2004

(65) Prior Publication Data
US 2007/0276421 A1    Nov. 29, 2007

(30) Foreign Application Priority Data

Jun. 20, 2003   (DE) .............................. 203 09 616 U

(51) Int. Cl.
*A61B 17/32*   (2006.01)

(52) U.S. Cl. ........................................ 606/167; 417/536

(58) Field of Classification Search .................. 606/166, 606/167; 417/212, 218, 221, 535, 536, 538
See application file for complete search history.

(56) References Cited

U.S. PATENT DOCUMENTS

| | | | | |
|---|---|---|---|---|
| 3,496,874 A | * | 2/1970 | Findlay | 417/383 |
| 3,622,251 A | * | 11/1971 | Allen | 417/471 |
| 4,234,107 A | * | 11/1980 | Gernlein | 222/309 |
| 4,551,146 A | * | 11/1985 | Rogers | 604/403 |
| 4,818,190 A | * | 4/1989 | Pelmulder et al. | 417/360 |
| 5,370,609 A | | 12/1994 | Drasler et al. | |
| 5,591,184 A | * | 1/1997 | McDonnell et al. | 606/167 |
| 5,871,462 A | * | 2/1999 | Yoder et al. | 604/22 |
| 5,931,647 A | | 8/1999 | Jacpbsen et al. | |
| 6,216,573 B1 | | 4/2001 | Patterson et al. | |
| 2001/0043874 A1 | | 11/2001 | Inoue et al. | |
| 2007/0276421 A1 | | 11/2007 | Pein | |

FOREIGN PATENT DOCUMENTS

| | | |
|---|---|---|
| EP | 0551920 | 7/1993 |
| WO | 2004112623 A3 | 12/2004 |

OTHER PUBLICATIONS

Bing Dictionary definition of "attached" as obtained Feb. 12, 2012; http://www.bing.com/Dictionary/search?q=define+attached&qpvt=define%3a+attached&FORM=DTPDIA.*

* cited by examiner

*Primary Examiner* — S. Thomas Hughes
*Assistant Examiner* — Jonathan W Miles
(74) *Attorney, Agent, or Firm* — Norris McLaughlin & Marcus, P.A.

(57) ABSTRACT

The invention relates to a water-jet device. The aim of the invention is to improve the adaptation of one such water-jet device to different applications. To this end, the piston cylinder unit (2) is connected to the eccentric drive device (20) in a separable manner and is embodied as an application-specific set with the suction line (4), the pressure line (7), and the operating handpiece (3). According to the invention, the piston cylinder unit (2) is especially provided with an annular fixing region (25) in which the sealing element of the piston (17) plunges and loses tension in the drawn-out end position of the piston (17), and the membrane (26) has sufficient free space to move.

6 Claims, 2 Drawing Sheets

WATER-JET DEVICE FOR SEPARATING A BIOLOGICAL STRUCTURE

BACKGROUND OF THE INVENTION

The invention relates to a water jet device.

Such water jet devices are used particularly in the field of human medicine.

Such a water jet device is described in EP 0 551 920 B1. This water jet device substantially comprises a pressure generator, a cylinder piston unit and a severing device in the form of a specific operating hand piece. In the cylinder space of the piston cylinder unit, a cartridge being filled with a sterile severing liquid is inserted in a form-fit manner. This cartridge, on the one hand, contacts the piston of the piston cylinder unit, and is connected to the operating hand piece via a pressure line, on the other hand. During operation, the pressure fluid of the pressure generator loads the piston cylinder unit and so the cartridge, and as a result of which the severing liquid is discharged from the cartridge toward the operating hand piece. There, the severing liquid comes out in the form of a fine jet of liquid. By separation of the severing liquid circuit from the pressure liquid circuit and by means of a special design of all instrument components of the severing liquid circuit a continuous chain of sterility is ensured.

However, due to the limited filling volume of the cartridge it turned out that such a water jet device is not suited for these cases of application which require a greater quantity of severing liquid. This disadvantage relates to all applications of plastic surgery, in particular liposuction. Another disadvantage is in that for specific cases of application, the uniformly emerging jet of liquid has to be pulsed with an auxiliary unit. This expense is relatively high.

From U.S. Pat. No. 6,216,573 B1 a water jet device has become known now which does not have these disadvantages. This water jet device comprises a higher situated storage container for the severing liquid, a piston pump and an operating hand piece. The higher situated storage container is connected to the piston pump via a descending line and a pressure line leads from the piston pump to the operating hand piece. For this purpose, the piston pump comprises a pump casing having the piston cylinder unit and an eccentric drive propelling the piston of said piston cylinder unit wherein a membraneous liquid bladder is inserted into the cylinder space of the piston cylinder unit, and the residual cylinder space is charged with a pressure liquid. The membraneous liquid bladder, on the one hand, is connected to the storage container via the descending line and to the operating hand piece via an opening check valve and via the pressure line, on the other hand. The membraneous liquid bladder is generally and alternately pressurized with overpressure or subpressure by the motion of the piston such that the severing liquid in the storage container is drawn in a pulsating manner and is subsequently fed in a pulsating manner toward the operating hand piece. However, this water jet device has disadvantages. Thus, the piston cylinder unit does not generate any defined and sharp severing jet due to the severing jet being mainly determined by the volume change of the liquid bladder, and this volume change is not reproducible because the liquid bladder is merely fixed by two liquid columns. The piston cylinder unit is not efficient enough either. Primarily, it has to do with the fact that the direction of the liquid stream arriving into the liquid bladder and the direction of the pressure liquid stream emerging from the liquid bladder are acting in opposite direction. This results in turning back of the liquid flow within the liquid bladder and so in turbulences and drop in pressure.

It is also disadvantageous that there are two separate liquid circuits again which are to be separated from each other with high expense due to the requirement of sterility. However, an important disadvantage is in that the piston cylinder unit and the eccentric drive are accommodated in a common pump casing which because of that becomes largely and heavily constructing and may only be used fixedly. This raises the price of manufacturing and restricts the functional range strongly since the volume of the liquid bladder is merely designed for a selected range of application. Adaptation of the piston cylinder unit to different cases of application having a greater need of severing liquid is not possible due to the compactness of the pump casing, and the use of a larger liquid bladder in the existing pump casing has to be ruled out because the liquid bladder and the piston cylinder unit have to be well-matched to each other.

As a result, the invention is based on the development of a water jet device according to type for severing a biological structure which is built up in accordance with the modular design principle, and which can be adapted to different cases of application by means of substitution of individual instruments.

The novel water jet device eliminates the abovementioned disadvantages of the prior art.

SUMMARY OF THE INVENTION

The particular advantage of the novel water jet device is in that the piston cylinder unit is designed as an individual assembly, and as a result becomes independently from the eccentric drive means. Thereby, it is possible for the piston cylinder unit to be manufactured in a simple and cost effective manner, and to assemble it with the appropriate pressure and suction lines and with the operating hand piece as a set. As a result, the set can be designed for a particular case of application, and can be substituted for another set in case of a different application.

This opens a wide field of application for the water jet device.

Then it is advantageous when the combination of the piston cylinder unit having the eccentric drive means will be designed as a plug-in coupling. This facilitates the action of substitution.

The particular design of the piston cylinder unit is quite suitable. Thus, in addition to the suction and pressure space this piston cylinder unit comprises a parked position space in which the sealing element of the piston in the extended position is submerging and releasing it. Because of that, the fundamental shape and as a result the sealing function remain maintained over a long storage period which often equals to several months and years. And so, the water jet device becomes more reliably in operation.

In addition, this parked position space offers the advantage for the fixed membrane to have sufficient free space for the motions. This allows a sequence of motions of the membrane without constraint during the piston motions, and as a result prolonging the operating life of the membrane.

It is suitable when the parked position space or at least the transition from the suction and pressure space is designed conically, so as to allow the sealing element to submerge in a careful manner into the suction and pressure space. This increases the operating life of the membrane either. It is of particular advantage when the cylinder casing and the piston of the piston cylinder unit is made of plastic, and when the sealing element of the piston is designed as a sealing lip machined on to the piston and projecting. This facilitates manufacturing in a considerable degree. An advantageous design of the pressure intake on the cylinder casing results in that a pressure tubule having projecting press ribs and a press sleeve encircling the pressure tubule are pressed into the cylinder casing. As a result, the pressure line is pushed into the space between the press sleeve and the pressure tubule, and is radially pressed together.

A simple installation of the pressure intake results from the suction intake and pressure intake being situated radially opposite to each another. Then, the pressure tubule can be inserted and pressed together from inside into the cylinder casing via the suction intake. The radially opposing arrangement of the suction intake and pressure intake is also of great advantage such that the entering suction stream and the exiting pressure stream are directed in the same direction. This avoids unnecessary pressure drop losses in the flow, and a high energy efficiency with it.

BRIEF DESCRIPTION OF THE DRAWINGS

The invention shall be explained in more detail according to an embodiment in which.

DETAILED DESCRIPTION OF THE INVENTION

Figure 1:
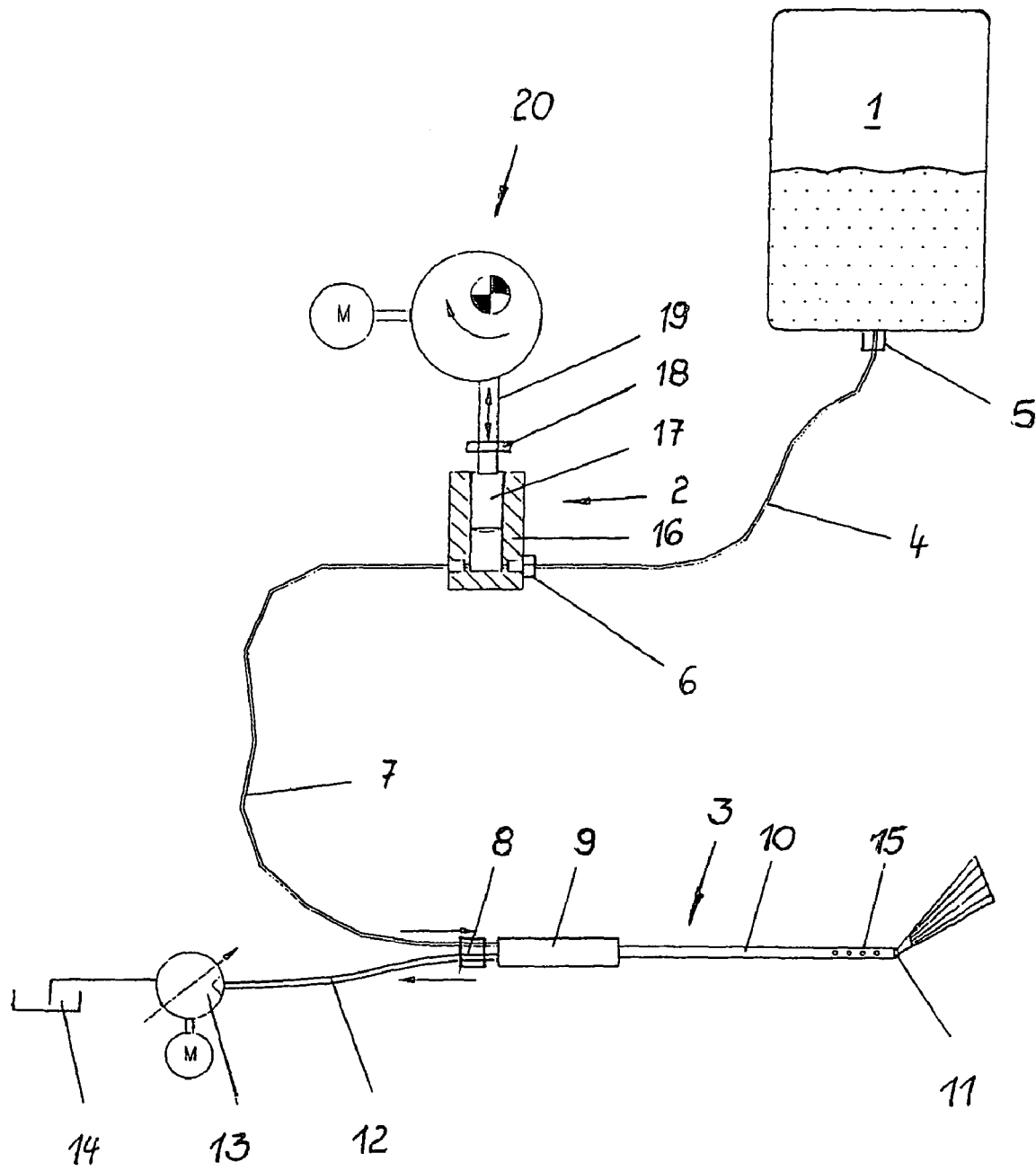
FIG. 1 shows a schematic representation of the water device.

According to FIG. 1, the water jet device for severing a biological structure comprises a storage container 1 for the severing liquid to be used, a piston cylinder unit 2 and an operating hand piece 3. On the occasion, the storage container 1 and the piston cylinder unit 2 are connected to each other via a suction line 4 wherein the suction line 4 is connected to the storage container 1 via a first plug-in coupling 5, and to the piston cylinder unit 2 via a second plug-in coupling 6. In contrast, the piston cylinder unit 2 is connected to the operating hand piece 3 via a pressure line 7 whereas the connection to the piston cylinder unit 2 is accomplished by means of a preferably permanent joint, and the connection to the operating hand piece 3 is accomplished by means of a third plug-in coupling 8.

The operating hand piece 3 in a well known manner comprises a hand piece 9 and a pressure and suction pipe 10. The pressure and suction pipe 10 has an internal pressure tubule with a discharging nozzle 11 situated at the end, which communicates with the pressure line 7 leading to the operating hand piece 3, and it has a suction pipe which sheathes the pressure tubule forming a ring channel, and which is connected to a receiving tank 14 via an exhaust line 12 and a driven exhaust pump 13. Furthermore, the suction pipe has radial exhaust apertures 15 being arranged in a circumferentially distributed manner to receive the separated tissue particles and collected severing liquid.

The piston cylinder unit 2 comprises a cylinder casing 16 and a piston 17 fitted with clearance in the cylinder casing 16. This piston 17 is connected to the actuating cam follower 19 of an eccentric drive means 20 via a plug-in coupling 18.

Figure 2:
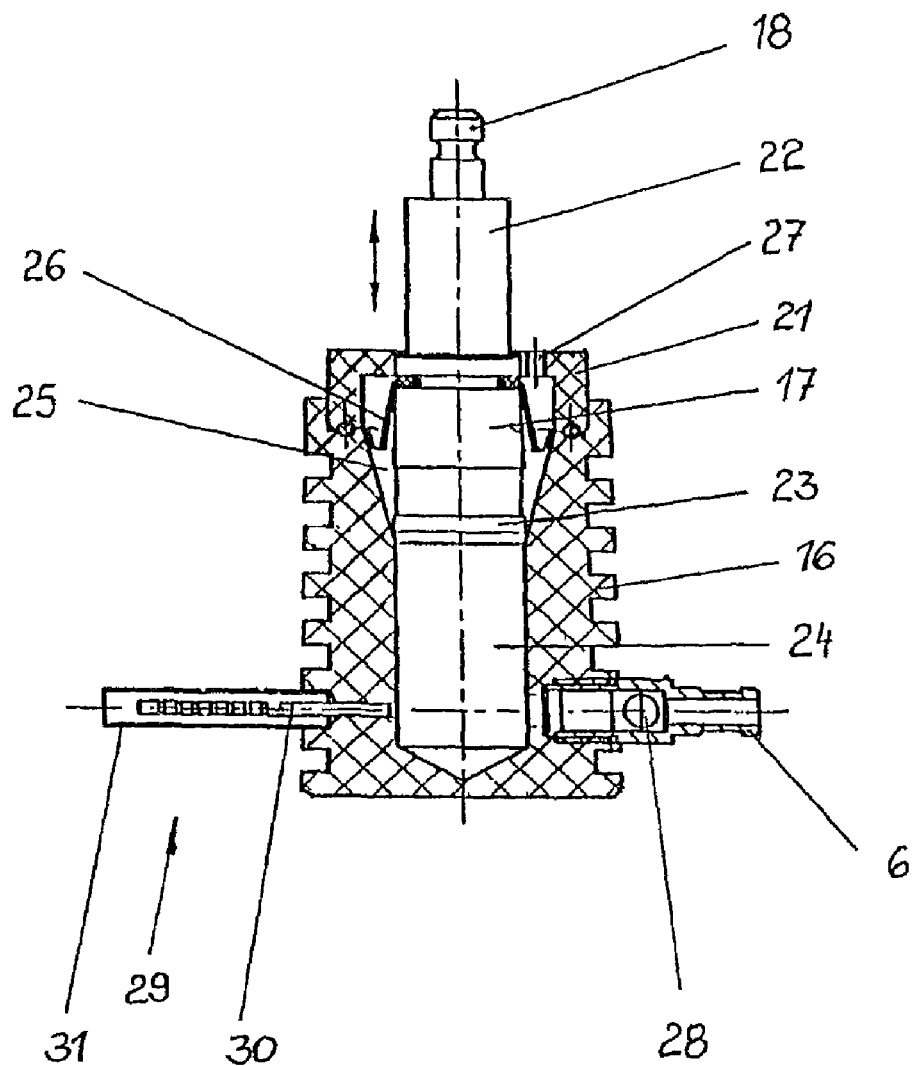
FIG. 2 shows a piston pump of the water jet device.

In FIG. 2, the piston cylinder unit 2 is illustrated in more detail and shows again the cylinder casing 16 and the piston 17 having its plug-in coupling 18 for the eccentric drive means 20. The cylinder casing 16 comprises a blind hole having a cylindrical portion which is close to the obturated end of the blind hole, and a conical portion which is in the area of the open end of the blind hole. On that occasion, the open end of the blind hole will be closed by means of the casing cover 21 in a pressure-sealed manner. The piston which penetrates the cylinder cap 21 with a coupling shank 22, on the one hand, and has a sealing lip 23, on the other hand, is inserted into the blind hole of the cylinder casing 16. As a result, the piston 17 with its sealing lip 23 and the blind hole of the cylinder casing 16 with its cylindrical portion form a suction and pressure space 24, whereas an annular parked position space 25 results between the circumference of the piston 17 and the conical portion of the blind hole. On that occasion, the length ratios between the piston 17 and the two portions of the blind hole of the cylinder casing 16 are selected such that the piston 17 in its extended final position is in abutment with the casing cover 21, and the sealing lip 23 is then taking up a position in the transition area from the cylindrical portion to the conical portion of the blind hole. In this position, the sealing lip 23 is some strain-free, however, still ensuring sufficient proofness between the suction and pressure space 24 as well as the parked position space 25. A membrane 26 is arranged between the piston 17 and the cylinder casing 16 which, on the one hand, is clamped between the cylinder casing 16 and the casing cover 21, and on the other hand, is fastened into an annular groove of the piston 17. This membrane 26 has such room to move then during cooperating with the parked position space 25 such that a sufficient stroke of the piston 17 is ensured without stoppage. The casing cover 21 is further equipped with an air compensation hole 27 which connects the volume varying air space between the membrane 26 and the casing cover 21 with the atmosphere.

The suction and pressure space 24, on the one hand, has a radial suction intake which is connected to the suction line 4 leading to the storage container 1 via the second plug-in coupling 6. A check valve 28 opening in the suction direction is inserted into this suction intake. Opposite the suction intake there is a radial pressure intake 29. This pressure intake 29 comprises a pressure tubule 30 which is pressed from inside into the cylinder casing 16 through the suction intake, and is equipped with external press ribs on the projecting end thereof. A press sleeve 31 which keeps an annular clearance toward the pressure tubule 30 free is externally pressed through this pressure tubule 30 into the cylinder casing 16. The pressure line 7 leading to the operating hand piece 3 is inserted into this annular clearance and pressed together with the pressure tubule 30 by means of force acting on the press sleeve 31.

In operation, the eccentric drive means 20 starts to move the piston 17 of the piston cylinder unit 2 in a pendulous motion wherein the piston 17 is alternately retracting and extending. While extending the piston 17, the suction and pressure space 24 increases such that a diminished pressure is generated which opens the check valve 28 in the suction line 4 and gets the severing liquid to suck from the storage container 1. This intake operation is supported in that the storage container is placed in a higher situated position, and thus use of the potential pressure of the severing liquid situated in the storage container 1 will be made. While retracting the piston 17, the suction and pressure space 24 decreases, and overpressure is generated which closes the check valve 28 in the suction line 4 and gets the severing liquid in the suction and pressure space 24 to feed into the pressure line 7 via the pressure tubule 30. From there, the severing liquid reaches to the operating hand piece 3 in a well known manner where it emerges as a concentrated or spread severing jet from the discharge nozzle 11. The emerged severing liquid and the split off tissue particles are drawn off simultaneously effected by the exhaust pump 13 and are deposited into a receiving tank 14.

The invention claimed is:

1. A water jet apparatus for severing a biological structure with a jet of severing liquid comprising water, the water jet apparatus comprising a storage container for the severing liquid, a piston-cylinder unit comprising a generally cylindrical opening formed in a casing having a wall and a bottom, a piston received in the cylindrical opening for reciprocal motion of the piston in the cylindrical opening with space remaining adjacent to the bottom of the cylindrical opening, the space functioning as a pressure space upon downstroke of the piston and as a suction space upon upstroke of the piston, opposite the bottom formed by the cylindrical opening, the cylindrical opening takes on a conical portion, an annular membrane extending between an inner periphery and an outer periphery, the outer periphery is attached to the conical portion of the generally cylindrical inner wall at a position in an upper zone of the piston-cylinder unit and the inner periphery is attached to the piston at a position in the upper zone of the piston-cylinder unit, the upper zone being defined by an annular space above the suction-pressured space, the membrane sealing interior of the piston-cylinder unit below the membrane from exposure to the ambient outside the piston-cylinder unit and the membrane being dimensioned so as to allow reciprocation of the cylinder and the annular space being dimensioned so as to allow movement of the membrane therein as the piston reciprocates and to accommodate the membrane when the piston is at rest at the end of downstroke, a manipulable operating device including an internal pressure tubule terminating in the jet, a suction line for conducting the severing liquid from the storage container to the suction-pressure space in the cylinder, a pressure line for conducting the severing liquid from the suction-pressure space in the cylinder to the operating device, a coupling for attaching an eccentric drive to and detaching the eccentric drive from the piston, the piston-cylinder unit together with the suction line, the pressure line and the operating device constituting a sub-assembly, wherein the suction line is attachable to and detachable from the storage container and the cylinder casing by means of a first and a second coupling and the pressure line is attachable and detachable from the manipulable operating device by a third coupling, a first opening through the cylinder casing, the first opening effecting communication of the pressure line with the suction-pressure space, a second opening through the cylinder casing, the second opening effecting communication of the suction line with the suction-pressure space the first and second openings being radially oriented and diametrically opposed and a check valve, opening in the suction direction, is inserted in the suction line.

2. The water jet apparatus according to claim 1, wherein at least a lowermost portion of the conical portion tapers inwardly in a downward direction toward the suction-pressured space.

3. The water jet apparatus according to claim 1, wherein the cylinder casing and the piston are constituted of plastic.

4. The water jet apparatus according to claim 1, further comprising a protruding sealing lip formed on the cylinder.

5. The water jet apparatus according to claim 1, further comprising a connecting device installed in the cylinder for connecting the pressure tube to the suction-pressure space, the connecting device comprising a pressure sleeve press fit into the first opening through the cylinder casing for effecting communication of the pressure line with the suction-pressure space, a pressure tubule concentrically received in the pressure sleeve and having external ribs spaced from an interior wall of the pressure sleeve by a distance corresponding to thickness of a wall of the pressure line, the wall of the pressure line at an end portion of the pressure line being gripped between the ribs of the pressure tubule and the interior wall of the sleeve.

6. The water jet apparatus according to claim 1, wherein the suction pipe of the manipulable operating device is connected via an exhaust line to a pump.

* * * * *